United States Patent [19]

Johnson

[11] Patent Number: 4,597,759
[45] Date of Patent: Jul. 1, 1986

[54] EXTENDABLE HYGIENIC PAD

[75] Inventor: Russell L. Johnson, Waupaca County, Wis.

[73] Assignee: Kimberly-Clark Corporation, Neenah, Wis.

[21] Appl. No.: 544,174

[22] Filed: Oct. 21, 1983

[51] Int. Cl.⁴ ............................................. A61F 13/16
[52] U.S. Cl. .................................... 604/385; 604/389; 604/390
[58] Field of Search ................... 604/385 R, 386, 398, 604/400, 378, 389, 390

[56] References Cited

U.S. PATENT DOCUMENTS

| | | |
|---|---|---|
| 1,705,194 | 3/1929 | Marinsky ............................ 604/400 |
| 3,654,929 | 4/1972 | Nilsson et al. ...................... 604/378 |
| 4,285,343 | 8/1981 | McNair ........................... 604/385 R |
| 4,376,440 | 3/1983 | Whitehead et al. ................. 604/387 |
| 4,536,181 | 8/1985 | Cook ................................... 604/387 |

Primary Examiner—C. Fred Rosenbaum
Assistant Examiner—Sherri E. Vinyard
Attorney, Agent, or Firm—Paul A. Leipold; Donald L. Traut; J. J. Duggan

[57] ABSTRACT

Hygienic pads such as sanitary napkins are provided with extensions, which can be attached to a central pad unit to increase the dimension in a direction determined by the user.

5 Claims, 2 Drawing Figures

EXTENDABLE HYGIENIC PAD

FIELD OF THE INVENTION

This invention relates to a hygienic pad such as a sanitary napkin. Particularly, this invention relates to a sanitary napkin or incontinence pad having a configuration which can be ultimately determined by the user.

BACKGROUND OF THE INVENTION

Hygienic pads, such as sanitary napkins and incontinence pads are usually designed to be symmetrical in configuration and of greater lengthwise than transverse dimension.

There have been some attempts to design such pads to provide a better contoured fit in the perineal area. One of the difficulties in attempting to design such a pad is that women have an almost infinite variety of body shape and muscle tone in the upper thigh region, and therefore, pads which provide superior comfort and protection for some women due to their configuration, may actually be deficient in these characteristics when worn by women of a different body type.

It has also been recognized that a certain percentage of the female population have extremely heavy flow during portions of the menstrual cycle. In addition, most women have heavy menstrual discharge early in the morning due to the retention of menses during sleep and at sudden discharge upon awakening.

Women have tried a variety of means to prevent staining and spotting during these heavy flow times. Some combine protection means such as using a tampon with a maxi-pad, or they will stack two pads. The latter has proven to be ineffective because only a small amount of the overflow from the top pad will reach the bottom pad and depending upon the positioning of the bottom pad very little will contact it due to the presence of the fluid impermeable baffle on the bottom of the first pad. Incontinence pads also are designed to be worn by the average user although, due to the nature of incontinence, there are a large variety of shapes and configurations available.

U.S. Pat. No. 2,683,457 describes the sanitary napkin having a recessed area positioned in the center, which is designed to receive a separate padlet positioned in the approximate center of the napkin. When the padlet is in place, the sanitary napkin is somewhat thicker in the center than on either end, but it is otherwise essentially of conventional configuration.

U.S. Pat. No. 2,771,882 discloses a flat hygienic pad that is designed to be segmented and each segment formed in a U-shaped configuration which is then used instead of tampon.

SUMMARY OF THE INVENTION

According to this invention a hygienic pad such as a sanitary napkin is provided with a primary elongate, absorbent element and at least one mating surface designed to engage a second absorbent element having a corresponding mating area. Thereby enabling the wearer to custom shape and design a hygienic pad for her particular purposes.

DETAILED DESCRIPTION OF THE INVENTION AND SUMMARY OF THE DRAWINGS

Figure 1:
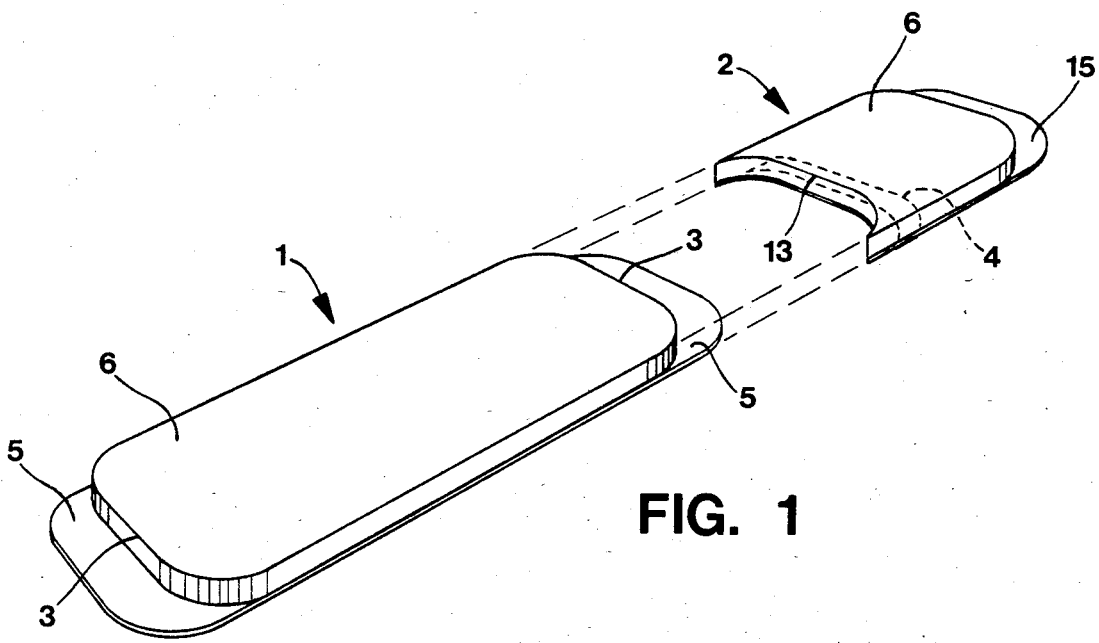
Figure 2:
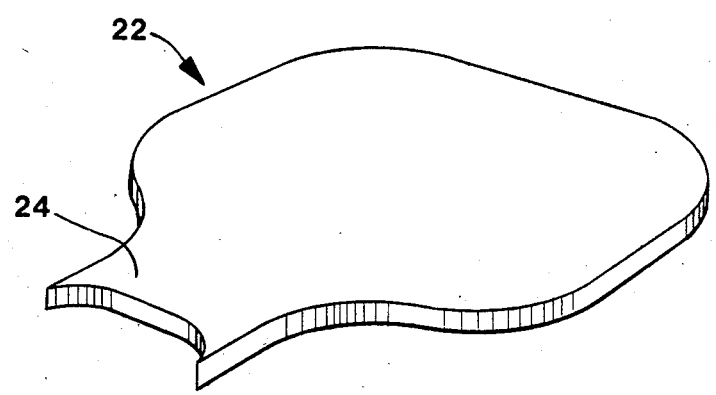

This invention may be more readily understood by reference to the drawings in which FIG. 1 is a perspective view of the first and second sections of the hygienic pad of this invention; and FIG. 2 is a perspective view of an alternative second section according to this invention.

As can be seen in FIG. 1, a first elongate section 1 has a fluid permeable cover 6 overlying an absorbent pad (not shown) on both the top side and end surfaces. The baffle 5 extends beyond the end of the wrapped absorbent pad and in combination with the curved end 3 forms a mating surface for attachment of a secondary absorbent section 2 which has a fluid pervious cover or wrap 6 overlying an absorbent layer (not shown) and a baffle segment 15 positioned on the bottom of the second section 2 and extending beyond one end. The baffle section 15 has an adhesive band 4, shown in phantom lines, designed to engage baffle extension 5 of FIG. 1 with mating end 13 designed to tightly about the mating end 3 to form a substantially continuous flat surface at the juncture of the two pads section.

The baffle section 15 may not be needed if the baffle of the elongate segment is of sufficent length to offer protection for most of the extension. The baffle of the second section 2 may not be needed in any event, because the fluid runoff at the end of the composite napkin may not be of sufficient volume to saturate the absorbent at the end and require the same type of baffle protection present at the bottom of the first elongate section.

In FIG. 1, the extension designed to provide a support surface for the adhesive attachment of the secondary absorbent section is made up of the extended baffle but, depending upon the particular pad construction may also include the wrap 6 which can be sealed to the baffle by ultrasonic means or the like as is well known in the art. The particular construction of the elongate pad 1 with regard to whether the wrap 6 forms part of the extension which is a portion of the mating surface is not particularly relevant to the concept of the invention. The wrap may also extend over the baffle on the bottom portion of the napkin as is well known in the art.

In FIG. 2, another configuration for the secondary section 22 is depicted and in this instance there is no baffle 15 extending beyond the back nonmating end of the pad. It is possible within the teachings of this invention to laterally extend the tongue portion 24 and change the mating surface so that the tongue extension is bifurcated to form legs which would add width to the composite hygienic pad at the end or ends of the first elongate section 1. It is also within the ambit of this invention to extend the composite pad in both longitudinal directions and the extensions need not be of the same geometrical configuration.

While is shown in FIG. 1, adhesive means are provided for the essentially continuous attachment of the components, other attachment means can be utilized although for the maximum benefit the intimate contact between the mating surfaces particularly at the top is desirable so that a continuous surface is exposed to fluid discharge.

With the teachings of this invention it is also possible to design a pad which is both a sanitary and incontinence absorbent depending upon the position and the configuration of each of the elements.

It should be noted that the first elongate section can function as a sanitary napkin by itself and at some time during use the component parts may be added as desired to ultimately change the shape of the napkin.

What is claimed is:

1. A sanitary napkin comprising:
 a primary pad containing fluid absorptive material, said primary pad having a top, a bottom, sides, a vertical thickness, a lateral width and a longitudinal length;
 a second pad containing fluid absorptive material; and
 means for engaging said second pad to said primary pad to thereby extend said primary pad along said width and length, this extension being maintained in use of the sanitary napkin wherein said primary pad further includes a fluid impervious baffle along said bottom, a portion of said baffle extending beyond a side of said primary pad along said longitudinal length, said second pad having a mating portion adapted to be received on said extended baffle portion, and adhesive means on said mating portion for fixing said mating portion to said extended baffle portion.

2. The sanitary napkin of claim 1 wherein said engagement means comprises a tongue extending beyond a side of said primary pad, and adhesive means on said second pad for affixing said second pad to said tongue.

3. The sanitary napkin of claim 1 wherein said side of said primary pad beyond which said baffle extends has a contour, and said second pad has a side adjacent said mating portion which has a contour which complements said primary pad contour such that the sanitary napkin has a substantially unbroken top surface.

4. A hygienic pad of the type having an absorbent layer with a top surface and a bottom surface, a fluid permeable wrap overlying the top surface and a fluid impermeable baffle adjacent the bottom surface, comprising:
 a principal hygienic pad having at least one attachment face located at its periphery; and
 at least one secondary hygienic pad having an opposed mating face adapted to engage the attachment face of the principal hygienic pad to attach said primary and secondary pads together, thereby varying the length or width of the principal hygienic pad.

5. A sanitary napkin comprising:
 an elongated primary pad containing fluid absorptive material, said pad having a top, a bottom and a pair of ends along a longitudinal axis;
 a second pad containing absorptive material; and
 means for engaging said second pad to said primary pad at one of said ends to thereby increase the longitudinal length of said sanitary napkin wherein said primary pad includes a fluid impervious baffle along said bottom, a portion of said baffle extending beyond a pad end, said second pad having a mating portion which overlies said baffle extension and mates with said pad end to form a substantially continuous top surface to the sanitary napkin, said mating porton including adhesive means to affix said second pad to said baffle extension.

* * * * *

UNITED STATES PATENT AND TRADEMARK OFFICE
CERTIFICATE OF CORRECTION

PATENT NO. : 4,597,759
DATED : July 1, 1986
INVENTOR(S) : R. L. Johnson

It is certified that error appears in the above–identified patent and that said Letters Patent are hereby corrected as shown below:

Column 1, Line 48, delete "it".

Column 2, Line 17, "about" should read "abut"

Column 4, Line 18, after "containing" insert --fluid--.

Signed and Sealed this

Twenty-fourth Day of March, 1987

Attest:

DONALD J. QUIGG

Attesting Officer

Commissioner of Patents and Trademarks